(12) United States Patent
Roehrig et al.

(10) Patent No.: US 8,086,015 B2
(45) Date of Patent: Dec. 27, 2011

(54) FACILITATING COMPUTER-AIDED DETECTION, COMPARISON AND/OR DISPLAY OF MEDICAL IMAGES BY STANDARDIZING IMAGES FROM DIFFERENT SOURCES

(75) Inventors: Jimmy R. Roehrig, Palo Alto, CA (US); Julian Marshall, Los Altos, CA (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 12/704,232

(22) Filed: Feb. 11, 2010

(65) Prior Publication Data

US 2010/0142793 A1    Jun. 10, 2010

Related U.S. Application Data

(63) Continuation of application No. 10/622,978, filed on Jul. 18, 2003, now Pat. No. 7,680,315, which is a continuation-in-part of application No. 09/992,059, filed on Nov. 21, 2001, now Pat. No. 7,054,473, and a continuation-in-part of application No. 10/079,327, filed on Feb. 19, 2002, now Pat. No. 7,072,498.

(51) Int. Cl.
*G06K 9/00*    (2006.01)

(52) U.S. Cl. .................................................. 382/132
(58) Field of Classification Search .................. 382/132
See application file for complete search history.

(56) References Cited

U.S. PATENT DOCUMENTS

| | | | | |
|---|---|---|---|---|
| 5,461,653 | A | * | 10/1995 | Parker .............................. 378/22 |
| 5,657,362 | A | * | 8/1997 | Giger et al. ...................... 378/37 |
| 5,740,267 | A | * | 4/1998 | Echerer et al. ................. 382/132 |
| 5,954,650 | A | * | 9/1999 | Saito et al. ...................... 600/425 |
| 6,058,322 | A | * | 5/2000 | Nishikawa et al. ............ 600/408 |
| 6,434,262 | B2 | * | 8/2002 | Wang ............................. 382/132 |

* cited by examiner

*Primary Examiner* — David Zarka

(57) ABSTRACT

The present invention is methods for processing medical images so as to remove certain effects of the physical characteristics of the object being imaged and/or of the apparatus used to form the images. The invention further provides for the formation of a standardized image from the processed image and for the use of the standardized image or the processed image in the training of computer-aided detection/diagnosis algorithms. These algorithms may then be used to detect abnormalities in other standardized or processed images derived from any of a variety of image acquisition systems.

5 Claims, 6 Drawing Sheets

FACILITATING COMPUTER-AIDED DETECTION, COMPARISON AND/OR DISPLAY OF MEDICAL IMAGES BY STANDARDIZING IMAGES FROM DIFFERENT SOURCES

CROSS-REFERENCE TO RELATED APPLICATION

This application is a continuation of 10/622,978, file Jul. 18, 2003, now U.S. Pat. No. 7,680,315 which is a continuation-in-part of application Ser. No. 09/992,059, filed Nov. 21, 2001 now U.S. Pat. No. 7,054,473 for "A Method and Apparatus for an Improved Computer Aided Diagnosis System," and application Ser. No. 10/079,327 filed Feb. 19, 2002, now U.S. Pat. No. 7,072,498 for "A Method and Apparatus for Expanding the Use of Existing Computer-Aided Detection Code" which applications are incorporated herein by reference.

The subject matter of the present application is related to commonly assigned U.S. Pat. No. 7,668,358 for "Model-Based Grayscale Registration of Medical Images". This application is incorporated herein by reference.

FIELD OF THE INVENTION

The present invention relates to facilitating computer-aided detection, comparison and/or display of medical images. A particularly useful application of the invention is in the field of radiographic mammography and the invention will be described in detail in that context. The invention may also be practiced in numerous other contexts.

BACKGROUND OF THE INVENTION

Mammography is a specialized form of radiography designed to detect the subtle changes in x-ray attenuation that are caused by cancerous tissue when x-rays irradiate the human breast. While there is presently no means for preventing breast cancer, early detection of the disease prolongs life expectancy and decreases the likelihood of the need for a total mastectomy. Radiographic mammography is currently the most common method of detecting and analyzing breast lesions. The American Medical Association, The American Cancer Society, and the American College of Radiology recommend yearly mammograms for women beginning at age 40.

Particular features in mammograms that are indicative of breast cancer include spiculated, or stellar-shaped, lesions and microcalcifications. While both features have a relatively high probability of being malignant, both features are also difficult to detect. To detect any feature at all, the x-ray attenuation of that feature must differ appreciably from that of its environment. In the case of cancerous tissue, there is very little difference in attenuation between cancerous tissue and the glandular tissue in which it is found at x-ray energies above about 35 keV and a difference of only about 10% at x-ray energies of about 20 keV. Detection of spiculated masses is further complicated by the presence in typical mammograms of myriad lines corresponding to fibrous breast tissue. In the case of microcalcifications, while they are almost radiopaque, they are usually very small and faint in a mammogram and it is very difficult to distinguish cancerous microcalcifications from numerous other artifacts that are of similar size and appearance.

A typical analog or film-based mammography system 100 is shown in FIG. 1. The system comprises an x-ray tube 110, upper and lower compression paddles 130,135 an anti-scatter grid 140, a screen-film unit 150, and a phototimer detector 160, all of which are mounted on a frame 170. The x-ray tube comprises a cathode 112, an anode 114 that is mounted on a shaft 116 and rotated by a motor 118, a tube port 120, a filter 122 and a collimator 124. The screen-film unit includes an x-ray film 152 and a fluorescent screen 154. Phototimer detector 160 measures the total exposure. A control system (not shown) controls the operation of the x-ray tube including the peak voltage and tube current and terminates operation when a desired exposure as measured by detector 160 has been reached. Advantageously, the control system also includes a subsystem for measuring the space between compression paddles 130, 135 and therefore the thickness of the breast.

To make a mammogram, a patient's breast is compressed between a lower surface 132 of the upper compression paddle 130 and an upper surface 137 of the lower compression paddle; and the x-ray tube is turned on. Motor 118 rotates anode 114 while high energy electrons bombard the rotating anode causing the anode to emit x-rays. Some of the x-rays are emitted through tube port 120 in the direction of the breast located between the two compression paddles. The x-rays are band pass filtered by filter 122 to eliminate x-rays of especially high or low energies and are collimated by collimator 124 to eliminate those x-rays traveling in unwanted directions. The remaining x-rays pass through the breast where they are selectively attenuated and are incident on the anti-scatter grid 140. The x-rays that pass through the anti-scatter grid then pass through the x-ray film with little interaction with the film and are incident on the fluorescent screen 154. The x-rays interact with the fluorescent material in the screen, causing this material to emit radiation that interacts with the x-ray film to produce the x-ray image. Some of the x-rays also pass through the fluorescent screen and are incident on the phototimer detector 160.

A variety of choices are available in the physical properties of these systems. The optimal x-ray energy range for these systems is about 17 to 23 keV. Within this range, molybdenum has characteristic x-ray peaks at 17.5 and 19.6 keV and rhodium has such peaks at 20.2 and 22.7 keV; and anodes made of one or the other of these elements are widely used. Typically, the tube port is made of beryllium which has low attenuation. The filters are typically made of the same material as the anode but a rhodium filter is also used with a molybdenum anode for imaging thicker and denser breasts.

Ideally, the mammography system forms on film 152 a projection image of the attenuation of x-ray photons that traveled on straight lines from the anode through the breast to the film. However, the distribution of photons incident per unit area on the film is not uniform. Absorption of photons within the anode creates a "heel effect" as a result of which the area of the film directly under the anode will receive significantly fewer photons per unit area than the area of the film under the cathode.

The photons may also be redirected by Compton or Rayleigh scattering and arrive at the film from many different angles other than angles corresponding to a straight line from the anode. Such scattered photons reduce the contrast in the mammogram. The amount of scatter in mammography varies with increasing breast thickness and breast area. For a typical 5 cm-thick breast, the contrast reduction due to scatter is on the order of 33%. To reject scatter, parallel linear grids with a grid ratio of 4:1 to 5:1 are commonly used. While the film is exposed, the grids are oscillated over a short distance to blur the grid lines. A cellular grid structure is also used in some systems to reject scatter in two dimensions.

Various screen film systems are available from suppliers such as Agfa, Fuji and Kodak. All of these systems have a single gadolinium oxysulfide phosphor screen which produces green light and a green-sensitive single emulsion film. A variety of different speed films are available; and the characteristic curves of optical density versus exposure of these films can be quite different. Typical characteristic curves for two screen-film systems are shown in FIG. 2. Of particular note, the contrast in an image is a function of the slope of the characteristic curve.

Recently, mammography systems have become available that use digital detectors in place of a screen-film system. These systems produce digital mammograms without the intervening steps of processing a film and then digitizing it. The digital systems introduce considerably more variability in the process conditions. In addition to replacing the screen film combination, they also use different anode targets (typically, tungsten) and possibly other filters.

In addition to variations in the physical properties of the mammography system, numerous operational parameters are within the control of the operator. These include the x-ray energy, typically specified in peak voltage (kVp), the exposure, typically specified in milli-Ampere-seconds (mAs), and the processing of the x-ray film. Another factor that clearly affects the optical density recorded on the film is the thickness of the breast being x-rayed and its density (or proportion of glandular tissue to total breast thickness). To a limited degree, the thickness of the breast being x-rayed can be controlled by the operator by adjusting the pressure exerted by the upper compression paddle.

Despite the large number of physical and operational variables that exist in mammography systems, these differences are not an issue when reading a single set of mammograms taken at the same time under the same conditions. In reading the mammograms, the radiologist's attention is focused on the relative difference between adjacent regions of the mammogram; and since the mammogram was made under one set of conditions; these conditions have little effect on relative differences. However, the radiologist frequently wants to compare one set of mammograms with another set of mammograms, for example, a set of mammograms taken the previous year for the same person. In this case, there may be substantial differences between the two sets, for example, because they were taken on different systems, or recorded on different films, or taken with x-rays of different energy, or for different exposures. Needless to say, there are also substantial differences between film-based mammograms and digital mammograms. Similar issues arise in analyzing mammograms of different persons.

Efforts have been made to address these problems by abstracting out at least some of the differences attributable to the physical and operational variables. In *Mammographic Image Analysis* (Kluver 1999), Ralph Highnam and Michael Brady describe how to correct and remove the effects of x-ray scatter, x-ray energy (kVp), exposure (mAs) and breast thickness. See also, their PCT application PCT/GB00/00617 filed Feb. 21, 2000 and published as publication WO 00/52641 on Sep. 8, 2000, which is incorporated herein by reference. The result is a completely physical description of the breast in terms of thickness and type of material—fat or glandular tissue. Their interest is in the glandular or interesting tissue and they call this description $H_{int}$, which is expressed in units of centimeters. A complete physical description of the breast would require a combination of $H_{int}$ and either the total breast thickness, $H_{tot}$, or the fat thickness, $H_{fat}$, where $H_{tot}=H_{int}+H_{fat}$.

However, the $H_{int}$ image is very difficult for the radiologist to interpret since it is radically different from the conventional image the radiologist has been trained to interpret. Moreover, the computations needed to produce the $H_{int}$ image are extensive and require substantial amounts of processing time.

Another approach is described in U.S. Pat. No. 6,516,045 for "Device and Method for Determining Proportions of Body Materials", which is incorporated herein by reference. As shown in FIG. 3, in this technique, two right-angled wedge-shaped reference materials 302, 304 are positioned alongside the breast 306 between the compression paddles. One wedge has the attenuation characteristics of fat. The other wedge has the attenuation characteristics of glandular tissue. The base of each wedge is the thickness of the breast. As a result, when the mammogram is formed, an image is created of the wedges as well as the breast and the optical density of the image of the wedges ranges continuously from a value corresponding to 100% fat to 100% glandular tissue. Since the shape of the wedges is known, the optical density of each point in the image of the wedges can be associated with a specific percentage of fat and glandular tissue. Then by matching each pixel of the breast image with the pixels of the wedge having the same optical density, the percentage of fat and glandular tissue at that pixel in the breast image can be determined.

Still another approach is described in the co-pending applications Ser. No. 09/992,059 for "A Method and Apparatus for an Improved Computer Aided Diagnosis System," and Ser. No. 10/079,327 for "A Method and Apparatus for Expanding the Use of Existing Computer-Aided Detection Code" of which the present application is a continuation-in-part. In those applications, various normalization techniques are described to remove the differences caused by different detectors. In particular, the applications describe a variety of techniques for equalizing the contrast response in which analytic expressions or "look-up" tables are developed that convert the response measured by one system to what the response would be if measured by another system. While these techniques facilitate the analysis and comparison of mammograms made using different detectors, they do not address differences arising from different exposure parameters or differences in breast thickness.

Another area in which it would be advantageous to compensate for differences arising from different exposure parameters or differences in breast thickness is in the development of algorithms for computer aided detection and diagnosis of abnormalities in medical images such as mammograms.

The algorithms that are presently used are heavily dependent on the training of the algorithms using groups of mammograms. See, for example, U.S. Pat. No. 5,491,627 to Zhang et al., U.S. Pat. No. 6,075,879 to Roehrig et al., and the above-referenced Ser. No. 10/079,327 for "A Method and Apparatus for Expanding the Use of Existing Computer-Aided Detection Code." At present, to obtain a sufficient number of mammograms for training purposes, the set of training mammograms includes mammograms formed on different mammographic systems. As a result, the performance of the computer aided detection system is not as great as it would be if the training had been performed on the same sized set of mammograms made on a single system. It would be advantageous to be able to train the detection algorithm using larger sets of mammograms made on effectively the same mammographic system.

SUMMARY OF THE INVENTION

The present invention is methods for processing medical images so as to remove certain effects of the physical characteristics of the object being imaged and/or of the apparatus used to form the images. The invention further provides for the formation of a standardized image from the processed image and for the use of the standardized image or the processed image in the training of computer-aided detection/diagnosis algorithms. These algorithms may then be used to detect abnormalities in other standardized or processed images derived from any of a variety of image acquisition systems.

BRIEF DESCRIPTION OF THE DRAWING

These and other objects, features and advantages of the invention will be more readily apparent from the following detailed description of the invention in which.

DETAILED DESCRIPTION OF THE INVENTION

Figure 4:
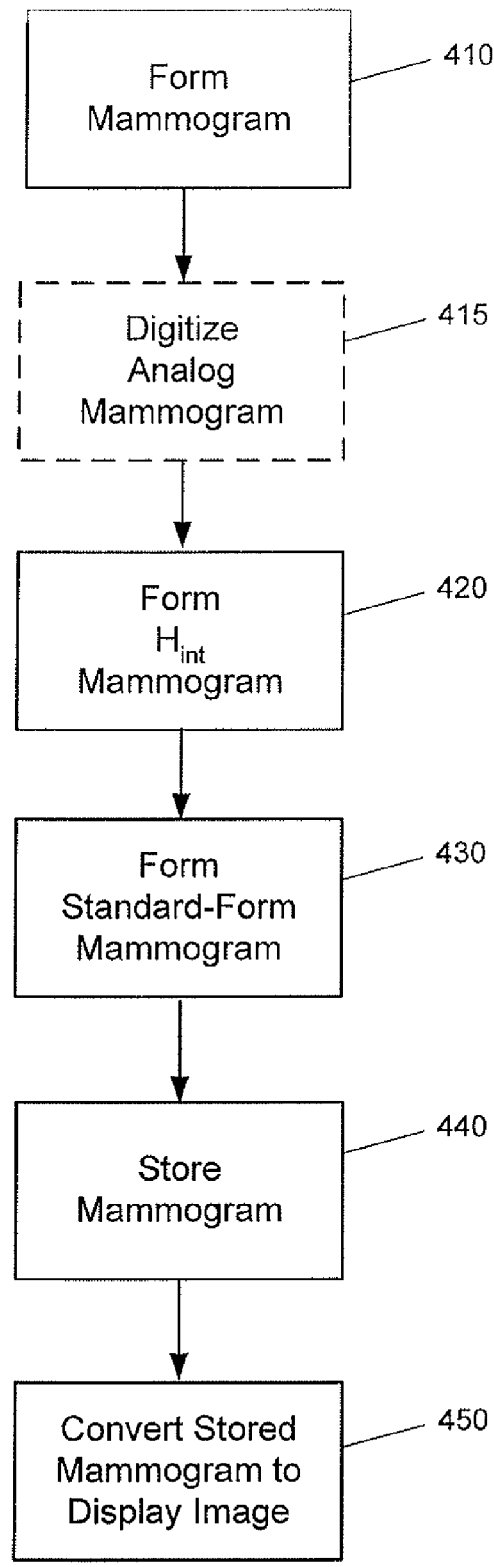
FIG. 4 is a flowchart depicting a first embodiment of the invention.

FIG. 4 is a flowchart depicting a first embodiment of the invention. At step 410 a mammogram is formed using either an analog mammography system such as that shown in FIG. 1 or a digital mammography system. If an analog system is used in step 410, the resulting mammogram film is then scanned at step 415 to convert the analog image into a digitized image. At step 420, the digital image formed in step 410 or the digitized imaged formed in step 415 is processed to remove at least one and preferably substantially all distinguishing effects related to the physical characteristics of the first mammography system and its operating parameters.

These effects may include effects arising from physical characteristics of the mammography system such as anode material, source to image distance, anti-scatter grid geometry, film characteristics, and screen film system. They may also include operating characteristics of the mammography system that may vary from patient to patient even when using the same mammography system such as x-ray energy, and magnitude and duration of exposure as well as physical differences between patients such as thickness and density of the breast being imaged. In addition, processing preferably is performed to measure the relative fat content of the breast being imaged.

The processing of the digital or digitized mammogram is preferably performed by a computer. Preferably, the processing performed is essentially the same as that detailed by Highnam and Brady in their book *Mammographic Image Analysis* and in their PCT patent application PCT/GB00/00617. As indicated above, extensive processing is necessary to remove the effects of the mammography system as well as to remove the effects of the fat content of the breast which is not interesting to the radiologist.

The result of the processing is an image representative of the physical characteristics of the breast that was imaged by the first mammography system and, in particular, representative of its glandular (non-fatty) tissue content. This image is referred to by Highnam and Brady as the $H_{int}$ (or interesting) image and comprises a two-dimensional array of numerical values representative of the thickness of glandular tissue at each point in the array.

At step 430, the processed image is converted from the $H_{int}$ image to a standard-form mammogram by calculating what the original mammogram would have looked like had it been made on a standard-form mammography system having a standard set of physical characteristics and a standard set of operating parameters. These calculations are essentially the reverse of the calculations used to form the processed image but using in this case the physical characteristics and operating parameters of the standard-form mammography system. For example, for the standard-form system, the x-ray energy preferably is set to 25 kVp, the exposure to 100 mAs, and the breast thickness to 5 cm. These parameters are preferred in view of the energy dependence of breast x-ray attenuation. Alternatively, the x-ray energy may be set at a value within the range 25-28 kVp and the exposure at a value within the range 20-200 mAs, and the thickness to a value within 4-6 centimeters. The processing required to form the standard-form image is extensive and preferably is performed by a computer.

At step 440, the standard form mammogram is then stored.

In like fashion, other digital or digitized mammograms formed by the same mammography system or by different mammography systems are similarly processed by the system of the present invention to form processed images from which have been removed the same effects related to the physical characteristics and operating parameters of the mammography system as well as to the fat content of the breast; and the processed images are converted to standard-form mammograms and stored.

The standard-form mammograms are then available to be compared at step 450. In all cases, the standard-form mammograms are free of the differences that otherwise would be present arising from the use of different mammography systems and/or different operating parameters in the formation of the mammogram. In the case where the standard-form mammograms are images of the same breast, the images will be essentially the same except for any physiological changes that have occurred in the breast between the time the first mammogram was taken and the time any later mammogram was taken.

Comparisons may be made using a variety of modalities such as computer work stations, film display systems, and images printed on paper. Again, there are considerable differences in the display characteristics of the different modalities and significant differences in the display characteristics of different suppliers' products in the same modality. Of particular interest are differences in brightness and contrast in the displayed images. Advantageously, these differences can be controlled to meet the needs of the user. For example, analytic expressions and/or look-up tables can be developed that relate pixel values of standard-form images stored at step 440 to levels of brightness on a particular manufacturer's work station, to levels of optical density in a film or to gray scale values in an image printed on paper by a laser printer. These expressions or look-up tables are then used at step 450 to convert the standard form images to images having the desired brightness and contrast in the display modality of choice.

Figure 1:
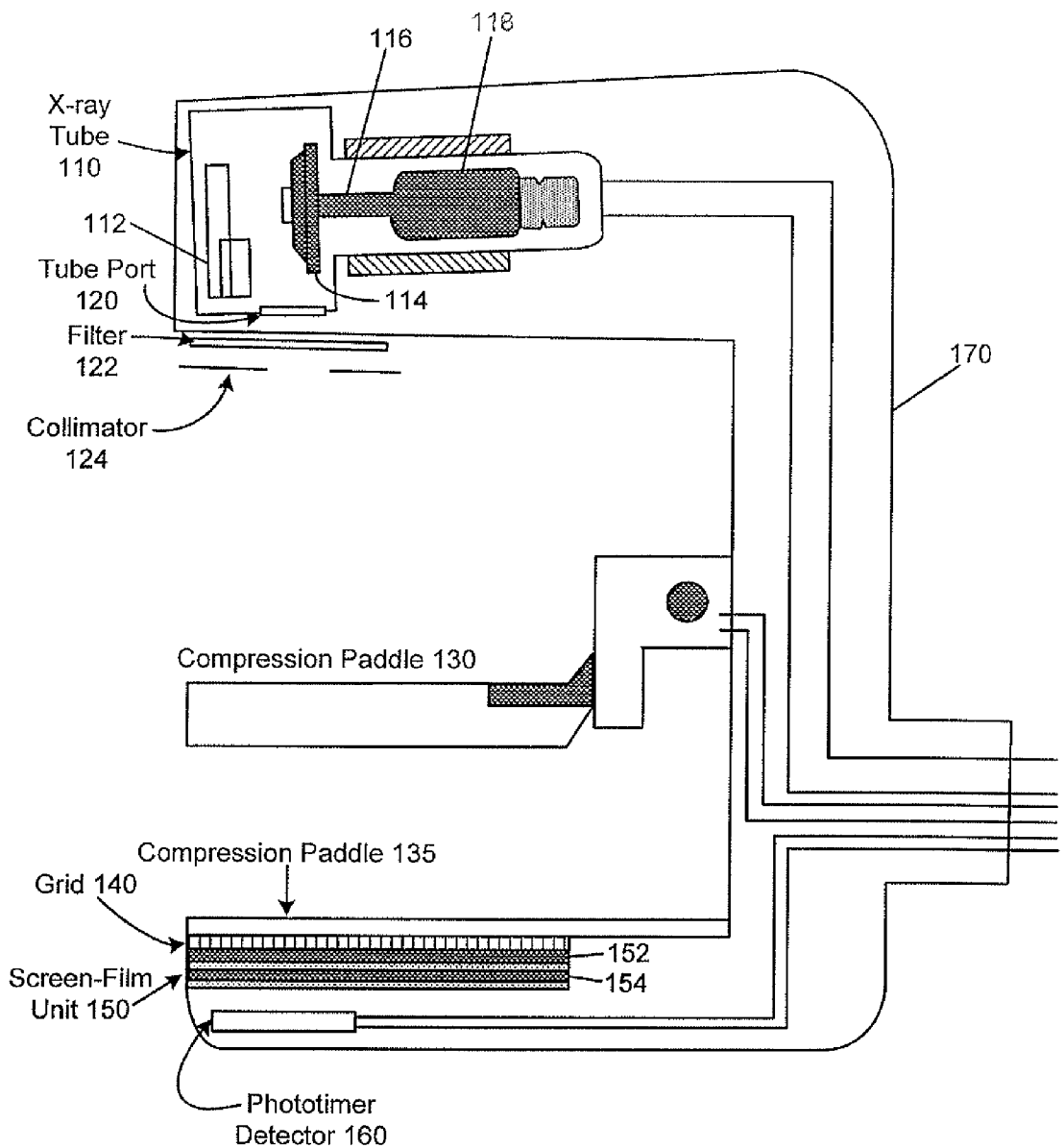
FIG. 1 is a schematic illustration of a prior art analog mammography system.

To understand how to obtain a purely physical description of the breast such as the $H_{int}$ image, a simplified example of computing $H_{int}$ is presented here for three hypothetical locations in a breast, including a first location that is 100% fat, a second location that is 50% fat and 50% glandular, and a third location that is 100% glandular. We will assume the breast is uniformly exposed to mono-energetic x-rays in a device such as shown in FIG. 1. We will assume further that the compression thickness $H_{tot}$ is uniform—i.e. the compression paddles are parallel. Actual computations to account for the true x-ray spectrum, and to correct effects such as tilt in the compression paddles, will be more complex than shown here, but the description below is adequate to describe the principle of how to derive the $H_{int}$ image from the exposure of the actual breast.

The intensity of x-ray penetrating material is given by Beer's law:

$$I_{out}=I_{in}\exp(-\mu\Delta h)$$

where $\mu$ is the attenuation of x-rays through matter, and $\Delta h$ is the thickness of the material. Let us suppose the attenuation of fat is given by $\mu_{fat}$ and the attenuation of glandular tissue is $\mu_{tissue}$. In reality the attenuation is also a function of energy of the x-ray, but here we will assume that the x-rays are mono-energetic and the attenuation can then be represented with a single number $\mu$.

Then the intensity after passing through $H_{tot}$ of a fatty section, an equal proportion of fat and tissue, and a pure tissue regions will be:

$$I_{in}\exp(-\mu_{fat}H_{tot})$$

$$I_{in}\exp(-(\mu_{fat}+\mu_{tissue})H_{tot}/2)$$

$$I_{in}\exp(-\mu_{tissue}H_{tot})$$

We assume that the exposure parameters are somehow available so that $I_{in}$ (in units of mAs or milliAmp-sec) is known, the values for attenuation $\mu$ in fat and tissue are known, and the thickness $H_{tot}$ has been measured. If the mammogram has been acquired on film/screen, these parameters are written onto the patient labels which appear on the margins of the films. Co-pending patent application Ser. No. 10/142,704 for "A Method and Apparatus to Associate User Data from a Radiograph" describes an automated technique for obtaining that information using optical character recognition (OCR). This application is incorporated herein by reference. If the mammogram has been acquired on a digital detector, the exposure parameters are entered into fields in the standard DICOM header which is created for each image.

Figure 2:
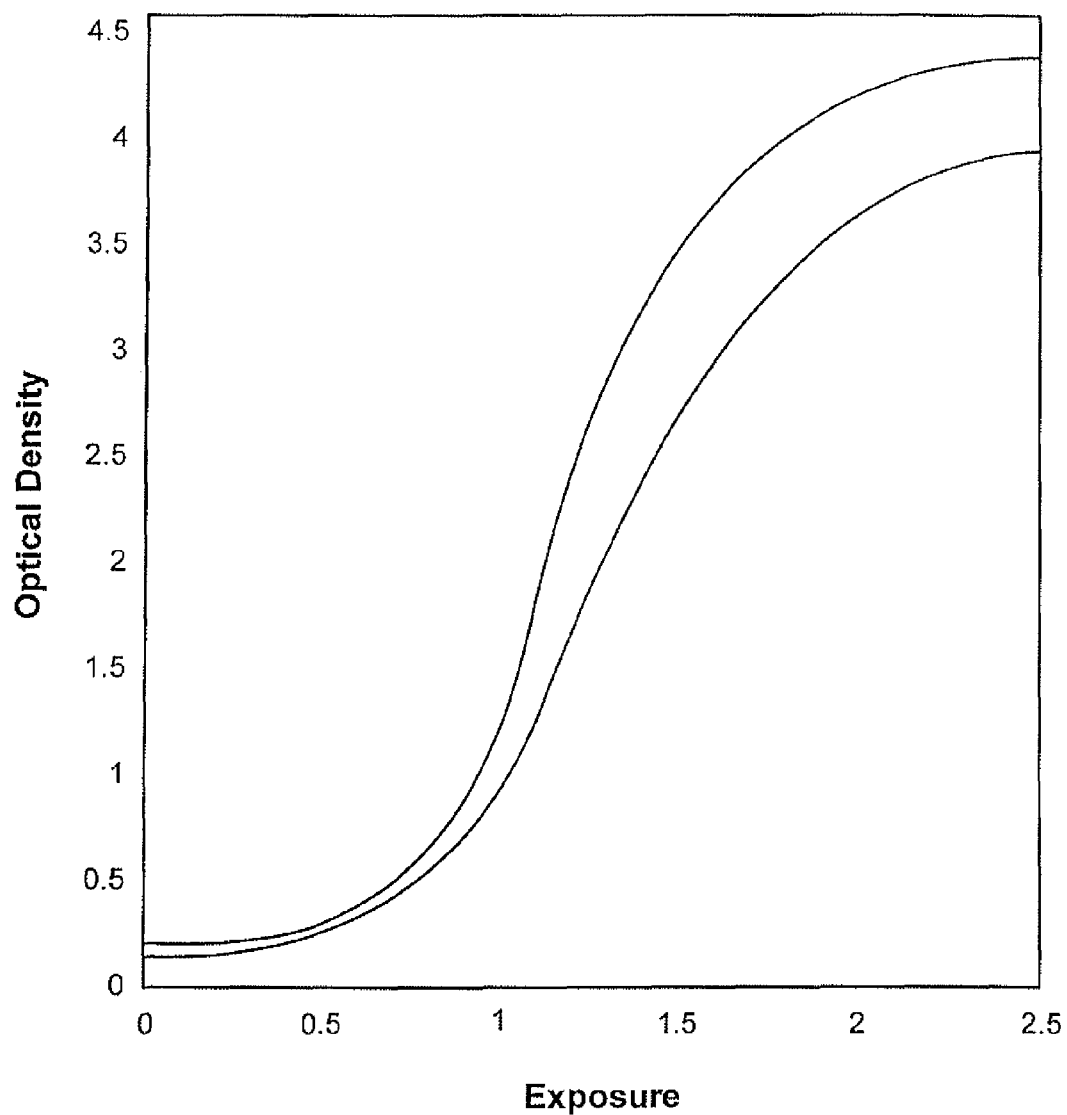
FIG. 2 is a depiction of the characteristic response of two radiographic mammography films.

The equations above relate the intensity of x-rays at the detector to the exposure and material characteristics. To actually perform any actual operations in the computer, we must also know how the intensity maps into pixel value in the computer image. This mapping is given by the equation $$PV=K\ln(I/I'),$$

which is the linear portion of the film response shown in the characteristic curves of FIG. 2. For purposes of this discussion, without loss of generality, let us ignore the constants K and I'. Then the pixel values for the image of the fatty section, an equal proportion of fat and tissue and a pure tissue region are:

$$PV_1=\ln(I)-\mu_{fat}H_{tot}$$

$$PV_2=\ln(I)-\mu_{fat}H_{tot}/2-\mu_{tissue}H_{tot}/2$$

$$PV_3=\ln(I)-\mu_{tissue}H_{tot}$$

Or, subtracting the constant factor $\ln(I)-\mu_{fat}H_{tot}$, and defining $\mu_\Delta=\mu_{tissue}-\mu_{fat}$, we can express the three pixel values as:

$$PV1=0$$

$$PV2=-\mu_\Delta H_{tot}/2$$

$$PV3=-\mu_\Delta H_{tot}$$

which are in the form $PV=\mu_{int}H_{int}$, where $H_{int}$ is 0 in the portion that is 100% fat, ¼ of $H_{tot}$ in the region with 50% tissue, and $1H_{tot}$ in the region with 100% tissue. Thus, the pixel values are a function of the thickness of the glandular or interesting tissue in the breast. This is essentially the "$H_{int}$" image as used by Highnam and Brady, and provides a representation of the mammogram which is free of the exposure parameters kVp, mAs, and compression thickness.

The standard image formed at step 430 differs from the $H_{int}$ image described in the above in that it will have the appearance of an x-ray mammogram with a known, "standard" thickness. Without loss of generality, we choose 5 cm as the "standard" thickness because this is a thickness that is quite common in actual mammograms. Further, we assume the mono-energetic x-ray energy to be 25 kVp, and the intensity to be I=100 mAs.

We convert the $H_{int}$ image to the standard-form "normal" image as follows. The minimum pixel value of this particular $H_{int}$ image is 0, which is the assigned value for pure fatty region of thickness 5 cm. Given a value of attenuation for fat at 25 kVp to be $\mu_{fat(25)}$, the $H_{int}$ image can be converted to a standard form image by adding $\ln 100\exp[\mu_{fat(25)}*(5-H_{int})]$ to each pixel value. The mapping of the $H_{int}$ image to the standard form image expressed by this exponential can be implemented in a look up table (LUT). If it is desired to represent the image as it would appear with other exposure parameters, i.e., other $H_{tot}$, intensity I, and attenuation corresponding to another kVp, this mapping can be implemented by:

$$PV_{new}=PV_{norm}+[\ln(I_{new})-\mu_{fat}(kVp)T],$$

which can be implemented in another LUT.

It remains to show how to map the appearance into the appearance of the standard form image of any given detector.

FIG. 2 shows the characteristic curves of two film brands used in mammography—Kodak Min-R2000 and Agfa HDR. These can be obtained from the manufacturers, or measured empirically by, for example, step wedges. The mapping from pixel value obtained from Agfa, for example, to Kodak Min-R2000 can be obtained directly from the two curves in FIG. 2, which can be implemented easily in a LUT. For example, an OD of 1.6 on Agfa would be mapped to approximately 2.4 to convert to a "Kodak" appearance. Similarly, a film/screen image from e.g., Kodak, can be converted to a digital detector which also has a characteristic response. Conversion from all types of mammographic image into all other types can be implemented in look up tables. Hence, we can in principle convert mammographic images from all sources into the common form and from the common form into any display form thus removing dependence on detector type.

Figure 3:
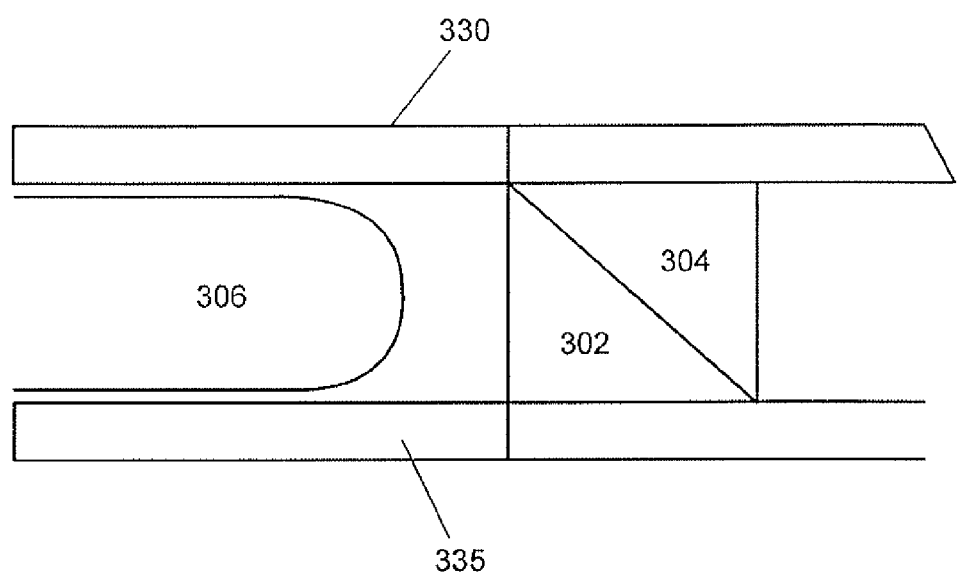
FIG. 3 is a schematic illustration of a prior art modification to a mammography system.
Figure 5:
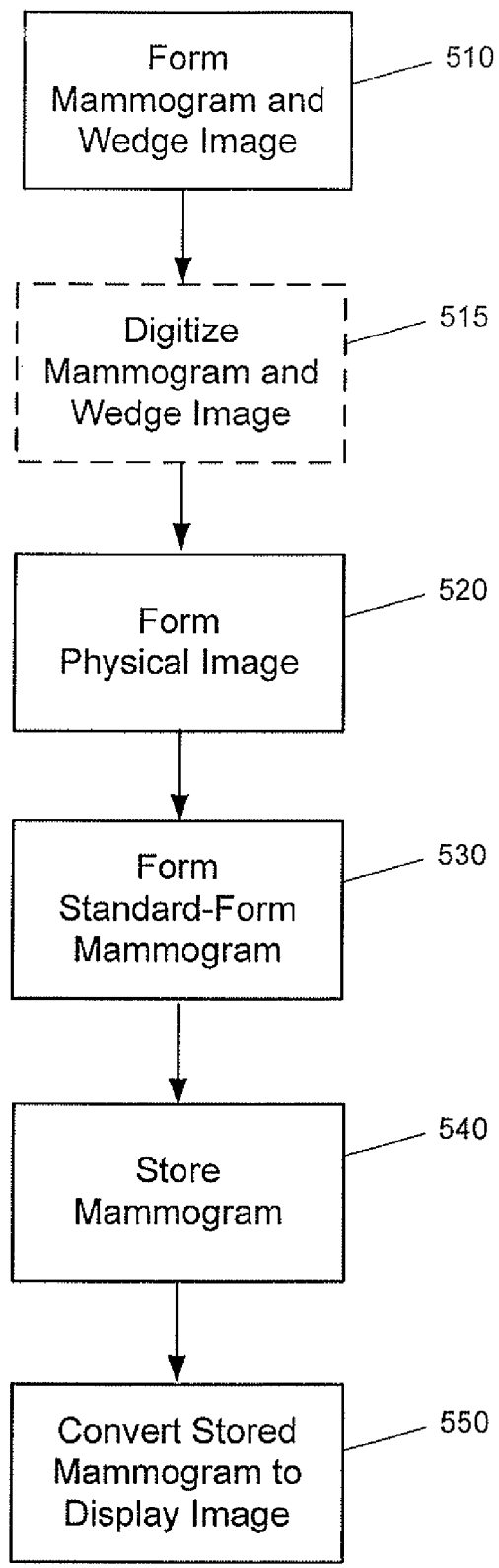
FIG. 5 is a flowchart depicting a second embodiment of the invention.

FIG. 5 is a flow-chart depicting a second embodiment of the invention. At step 510 a mammogram is formed using either an analog mammography system or a digital mammography system. Two wedge-shaped materials as illustrated in FIG. 3 are irradiated at the same time as the breast and their images are formed alongside the breast on the mammogram. If an analog mammography system is used in step 510, the mammogram film is then digitized at step 515 by a scanner to produce a digitized image of pixel values.

Whether formed directly by a digital mammography system in step 510 or by digitizing a file in step 515, the portion of the resulting image that is the image of the wedges will have pixel values ranging from a first value corresponding to 100% fatty tissue to a second value corresponding to 100% glandular tissue; and each pixel value in the image of the breast between the first and second values will be associable with a specific percentage of fatty and glandular tissue.

At step 520, a look-up table is created associating each pixel value in the image of the wedge with a specific percentage of fat and glandular tissue; and the pixel values in the digital or digitized image of the breast are converted to an image representative of the physical characteristics of the breast (i.e., percentage of fatty and glandular tissue) by using the table to convert pixel values in the breast image to percentages.

The physical image may then be used in the same fashion as the processed image produced at step 420 in the first embodiment. In particular, the physical image may be converted at step 530 to a standard form mammogram using a standard set of exposure parameters such as a peak energy level of 25 kVp and an exposure of 100 mAs for a breast having a thickness of 5 cm. The standard form mammogram may then be stored at step 540. Additional standard form mammograms may likewise be made and stored and any of these mammograms may later be retrieved at step 550 for display and comparison on suitable display modalities.

In addition to facilitating the comparison of mammograms, the present invention also facilitates the analysis of mammograms in computer aided detection and diagnosis systems. As indicated above, the algorithms used in such systems are typically trained on a large number of mammograms and this typically means that the mammograms were made on more than one mammography system.

In accordance with another embodiment of the present invention, algorithms are trained either on standard-form images or on physical images and mammograms are analyzed by applying the algorithm to either the standard-form image or the physical image of the mammogram.

Figure 6:
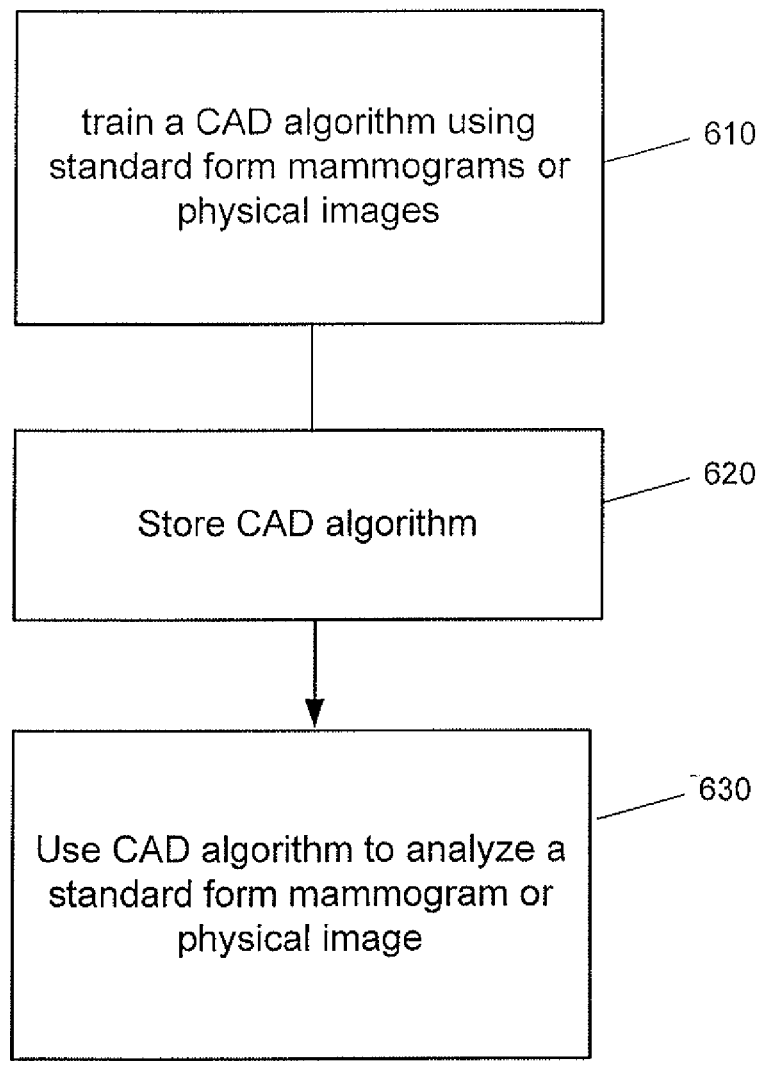
FIG. 6 is a flowchart depicting a third embodiment of the invention.

FIG. 6 is a flowchart depicting this embodiment of the invention. At step 610, a group of mammograms that have been converted to standard form images by the method of FIG. 4 or by the method of FIG. 5 are used to train a computer aided detection or diagnosis (CAD) algorithm. Advantageously, this group of mammograms is relatively large and is derived from a multiplicity of different mammography systems. For example, the group may include 100 mammograms made on each of four different systems. However, because the differences in the mammograms arising from differences in the different mammography systems have been removed as a result of the methods of FIG. 4 or FIG. 5, the group of mammograms appears to the training algorithm as one large set of mammograms from the same system. At step 620, the CAD algorithm is stored.

At step 630 the CAD algorithm is used to analyze a mammogram that has been made on any mammogram system and then converted to a standard form mammogram.

Alternatively, the training of the CAD algorithm could be performed on the physical images of the group of mammograms formed at step 420 or step 520 in which case the analysis of the mammogram would be performed on its physical image.

By using either standard form mammograms or physical images to train the CAD algorithm and then analyzing the standard form mammogram or physical image, only one CAD algorithm is needed. Moreover, a much larger number of mammograms are available to train the CAD algorithms.

FIG. 7A is a reproduction of a mammogram formed by a conventional mammography system. FIG. 7B is a reproduction of a mammogram formed by the method of FIG. 5 and converted to a standard form. The image of FIG. 7B has been processed to minimize the effect of any fat content in the breast image. A comparison of regions 710A and 720A in FIG. 7A with regions 710B and 720B in FIG. 7B reveals that features that are essentially indistinguishable in regions 710A and 710E are readily revealed in regions 720A and 720B.

What is claimed:

1. A method for processing mammographic images comprising the steps of:
   processing a plurality of digital or digitized mammograms formed by different x-ray mammography systems to remove distinguishing effects of each mammography system;
   transforming, with a computer, each processed mammogram into a standard-form x-ray mammogram having a first standard x-ray voltage parameter and a first standard exposure parameter, wherein at least one of the first standard x-ray voltage parameter and first standard exposure parameter differs from at least one of an x-ray voltage parameter and exposure parameter of at least one of the digital or digitized mammograms;
   storing said standard-form x-ray mammograms whereby visual comparison of x-ray mammograms taken by different x-ray mammography systems is facilitated by comparing standard-form x-ray mammograms derived from mammograms taken by the different x-ray mammography systems.

2. The method of claim 1 wherein the processing removes distinguishing effects of at least one of an x-ray voltage, an exposure voltage and a compression thickness.

3. The method of claim 1 wherein an x-ray image of a reference material and one of the mammograms are formed under a set of conditions, said reference material having known x-ray attenuation characteristics representative of different percentages of fat content, said method further comprising the step of identifying fat content in the one of the mammograms by comparing exposure values in the one of the mammograms with exposure values on the x-ray image of the reference material.

4. The method of claim 1 wherein the standard x-ray voltage parameter is in the range 25-28 peak voltage (kVp).

5. The method of claim 1 wherein the standard exposure is in the range 20-200 milli-Ampere-seconds.

* * * * *